(12) United States Patent
Yang

(10) Patent No.: US 12,670,644 B2
(45) Date of Patent: Jun. 30, 2026

(54) DATA PROCESSING METHOD FOR DETECTOR OF MEDICAL DEVICE, COMPUTER DEVICE AND STORAGE MEDIUM

(71) Applicant: SHANGHAI UNITED IMAGING HEALTHCARE CO., LTD., Shanghai (CN)

(72) Inventor: Peng Yang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 398 days.

(21) Appl. No.: 18/226,182

(22) Filed: Jul. 25, 2023

(65) Prior Publication Data

US 2024/0029325 A1     Jan. 25, 2024

(30) Foreign Application Priority Data

Jul. 25, 2022     (CN) .......................... 202210879541.0

(51) Int. Cl.
*G06T 12/10* (2026.01)
*A61B 6/00* (2006.01)

(52) U.S. Cl.
CPC ............ *G06T 12/10* (2026.01); *A61B 6/5258* (2013.01); *G06T 2210/41* (2013.01)

(58) Field of Classification Search
CPC .. G06T 11/005; G06T 2210/41; A61B 6/5258
USPC ....................................................... 382/131
See application file for complete search history.

(56) References Cited

U.S. PATENT DOCUMENTS

| 6,351,519 | B1 | | 2/2002 | Bonk et al. |
| 6,525,769 | B1 | * | 2/2003 | Thomas ................. H04N 25/63 |
| | | | | 348/241 |
| 8,622,302 | B2 | * | 1/2014 | Olmstead ........... G06K 7/10722 |
| | | | | 235/462.01 |
| 8,894,280 | B2 | * | 11/2014 | Topfer ................... A61B 6/585 |
| | | | | 250/252.1 |
| 9,195,899 | B2 | * | 11/2015 | Topfer ................... H04N 25/68 |

(Continued)

FOREIGN PATENT DOCUMENTS

| CN | 108124079 | A | 6/2018 |
| CN | 108903962 | A | 11/2018 |

(Continued)

OTHER PUBLICATIONS

STMicroelectronics "Dark calibration correction for high temperatures on VG5661, VD5661, VG5761, VD5761, VD6763, VG1762, and VD1762". Rev 2. Jun. 2022. (Year: 2022).*

(Continued)

*Primary Examiner* — Jennifer Mehmood
*Assistant Examiner* — Eric James Shoemaker

(57) ABSTRACT

The present disclosure relates to a data processing method for a detector of a medical device, which includes: obtaining a plurality of dark current values of at least one detector channel of a detector within a preset time period, adjusting the plurality of dark current values based on a preset scanning precision to determine a plurality of adjusted dark current values, and determining a dark current compensation value corresponding to the at least one detector channel based on the plurality of adjusted dark current values.

20 Claims, 6 Drawing Sheets

(56)                    References Cited

U.S. PATENT DOCUMENTS

| | | | | |
|---|---|---|---|---|
| 10,416,324 B2 * | 9/2019 | Cao | .......................... | G01T 1/247 |
| 2020/0297294 A1 * | 9/2020 | Tuch | .................. | A61B 1/00009 |

FOREIGN PATENT DOCUMENTS

| | | | | |
|---|---|---|---|---|
| CN | 110855915 A | 2/2020 | | |
| CN | 111436963 A | 7/2020 | | |
| EP | 2148500 A1 * | 1/2010 | ............. | H04N 25/63 |

OTHER PUBLICATIONS

Evangelos Matsinos, Wolfgang Kaissl. "The dual-gain mode: a way to enhance the dynamic range of X-ray detectors" Jul. 4, 2006. arXiv:physics/0607021. (Year: 2006).*
Office Action (CN Application No. 2022108795410) , dated Nov. 28, 2024, 9 pages.

* cited by examiner

DATA PROCESSING METHOD FOR DETECTOR OF MEDICAL DEVICE, COMPUTER DEVICE AND STORAGE MEDIUM

CROSS REFERENCE TO RELATED APPLICATIONS

The present application claims the priority to Chinese Patent Application with No. 202210879541.0, entitled "Data Processing Method and Apparatus for Detector of Medical Device, Computer Device and Storage Medium" and filed on Jul. 25, 2022, the content of which is incorporated herein by reference in its entirety.

TECHNICAL FIELD

The present disclosure relates to the field of medical imaging technology, and particularly to a data processing method for a detector of a medical device, a computer device and a storage medium.

BACKGROUND

Medical imaging devices are important tools for determining human health status in modern medicine. At present, common medical imaging devices include a computed tomography (CT) scanner, a digital radiography (DR) imaging device, and a computed radiography (CR) device, etc. The CT scanner, for example, needs to collect the real-time scanning data of a specified portion through a CT detector when performing a CT scan. However, with the increasing demand for situations of a low dosage or a special scenario, the requirements for the CT scanner detector in terms of precision of the analog-to-digital conversion (ADC), electronic noise, and photodiode dark current are increasing.

SUMMARY

A first aspect of the present disclosure provides a data processing method for a detector of a medical device. The method includes obtaining a plurality of dark current values of at least one detector channel of the detector within a preset time period, adjusting the plurality of dark current values based on a preset scanning precision to determine a plurality of adjusted dark current values, and determining a dark current compensation value corresponding to the at least one detector channel based on the plurality of adjusted dark current values.

In some embodiments, the adjusting the plurality of dark current values based on the preset scanning precision to determine the plurality of adjusted dark current values includes determining an actual scanning precision based on the plurality of dark current values, determining a correction parameter based on the preset scanning precision and the actual scanning precision, and adjusting the plurality of dark current values based on the correction parameter to obtain the plurality of adjusted dark current values.

In some embodiments, the adjusting the plurality of dark current values based on the correction parameter to obtain the plurality of adjusted dark current values includes adding low-order bits of zero to the plurality of dark current values respectively to obtain the plurality of adjusted dark current values, the number of the low-order bits of zero being equal to the correction parameter.

In some embodiments, the determining the dark current compensation value corresponding to the at least one detector channel based on the plurality of adjusted dark current values includes determining an average value of the adjusted dark current values, and determining the dark current compensation value according to the average value of the adjusted dark current value.

In some embodiments, the obtaining the plurality of dark current values within the present time period includes obtaining a plurality of output data values of the at least one detector channel under a non-exposure condition, and performing an analog-to-digital conversion based on the plurality of output data values to obtain the plurality of dark current values.

In some embodiments, after determining the dark current compensation value corresponding to the preset time period based on the plurality of adjusted dark current values, the data processing method further includes obtaining scanning data values of the at least one detector channel, determining corrected scanning data values based on the scanning data values and the dark current compensation value, and performing an image reconstruction based on the corrected scanning data values to obtain a scanning image.

In some embodiments, the determining the corrected scanning data values based on the scanning data values and the dark current compensation value includes performing a differencing correction on the scanning data values based on the dark current compensation value to determine the corrected scanning data values.

In some embodiments, before performing a differencing correction on the scanning data values based on the dark current compensation value, the data processing method further includes adjusting a scanning precision of the scanning data values such that the adjusted scanning precision is consistent with the that of dark current compensation value.

In some embodiments, the at least one detector channel includes two or more detector channels with different actual scanning precisions, and the preset scanning precision is larger than at least one of the actual scanning precisions.

In some embodiments, the preset scanning precision is equal to the largest one of actual scanning precisions.

A second aspect of the present disclosure provides a computer device, which includes a processor and a memory storing a computer program. When executing the computer program, the processor performs a data processing method according to the first aspect of the present disclosure.

A third aspect of the present disclosure provides a computer-readable storage medium having a computer program stored therein. The computer program, when executed by a processor, causes the processor to perform a data processing method according to the first aspect of the present disclosure.

DETAILED DESCRIPTION

Figure 1:
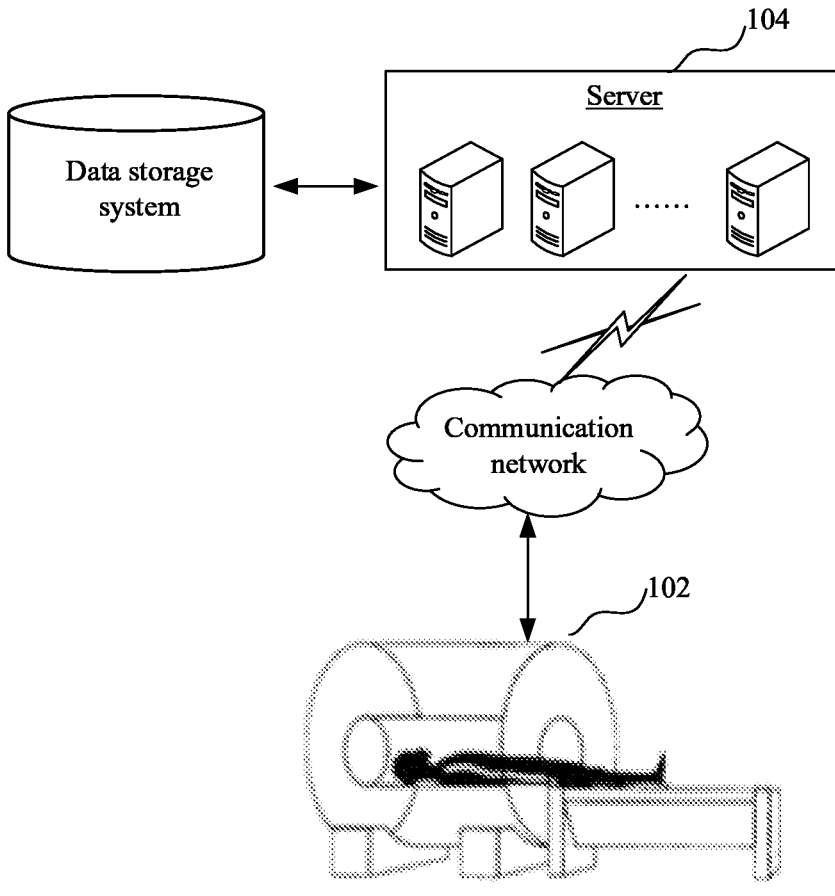
FIG. 1 is an application environment diagram of a data processing method for a detector of a medical device according to an embodiment of the present disclosure.

In order to make the purpose, technical solution and advantages of the present disclosure clearer, the present disclosure will be described in further detail in conjunction with the accompanying drawings and embodiments. It should be appreciated that the specific embodiments described herein are merely used for illustrating the present disclosure, rather than limiting the present disclosure.

A Computed Tomography (CT) device includes a tomography device and a computer system. Specifically, the tomography device may include a tube capable of generating an X-ray beam and a CT detector configured to receive and detect the X-ray. The computer system may include a data acquisition system, a central processing system, and a console, etc. In the specific scanning process, accurately collimated X-ray beams, γ-rays, ultrasonic waves, etc. can be utilized for performing a scan around a layer of a human body with a certain thickness, together with a highly sensitive detector. The X-ray transmitted through the layer is received by the detector, and is then converted into visible light which is then converted into an electrical signal by photoelectric conversion. The electrical signal is then converted into digits by an analog-to-digital converter, and the digits are inputted into a computer for processing.

A dark current is defined as a leakage current in the detector in the absence of incident light, which is one of main indicators of the detector. In the CT detector, the presence of the dark current may affect the final CT imaging quality, resulting in artifacts in the CT image.

According to a type of CT scanner known to the applicant, in order to eliminate the artifact in the CT image caused by the dark current, multiple dark current values are obtained through multiple different CT detector channels. The multiple dark current values are then averaged, and the average value is taken as a dark current compensation value. In the subsequent actual scanning process, the actual scanning values are compensated with the dark current compensation value to eliminate the impact of the dark current. The precision of the dark current is usually less required, but for a small part of CT scans, a higher precision of the dark current is required. When the dark current precision does not meet the requirement, the required dark current compensation value of the detector channel deviates from the actual dark current compensation value, which may have a significant impact on the CT image reconstruction and results in ring artifacts in the finally obtained CT image.

In the situation of low dosage or special application, the CT system has higher requirements for the analog-to-digital conversion (ADC) precision, the electronic noise, and the photodiode (PD) dark current. Due to the characteristics of the scanning mode of the CT system, the corresponding CT image is composed of data according to a plurality of time periods. When the ADC precision and electronic characteristics are unsatisfactory and the dark current values are large, the image noise may increase. Therefore, it is necessary to collect the dark current values within the multiple time periods before the scanning of the CT system, and calculate an average value of the dark current values. The scanning data in the actual scanning process is compensated with the average value which serves as a dark current compensation value.

In a dark current compensation method known to the applicant, for a single CT detector channel, the dark current values within the multiple time periods have the same numerical precision. For different scanning channels, however, precisions of multiple dark current values may be different, which may lead to an error in the compensation value of the dark current value and cause ring artifacts in the final CT image. In a special scanning, especially a situation of low dosage, the error of the dark current compensation values of different channels may have a significant impact on the CT imaging result.

A data processing method for a detector of a medical device provided by embodiments of the present disclosure may be applied to the application environment shown in FIG. 1. A terminal 102 communicates with a server 104 through a communication network. A data storage system may store data that the server 104 needs to process. The data storage system may be integrated in the server 104, or may be placed in a cloud or other network servers. Specifically, a plurality of dark current values in a digital circuit within a preset time period may be obtained by terminal 102. The plurality of dark current values in the digital circuit are then adjusted in the server 104 based on a preset scanning precision, and a plurality of adjusted dark current values are determined. A dark current compensation value corresponding to the at least one detector channel is determined based on the plurality of adjusted dark current values. The terminal 102 may be a scanning device for a variety of medical imaging devices. The server 104 may be implemented by an independent server or a server cluster including a plurality of servers.

Figure 2:
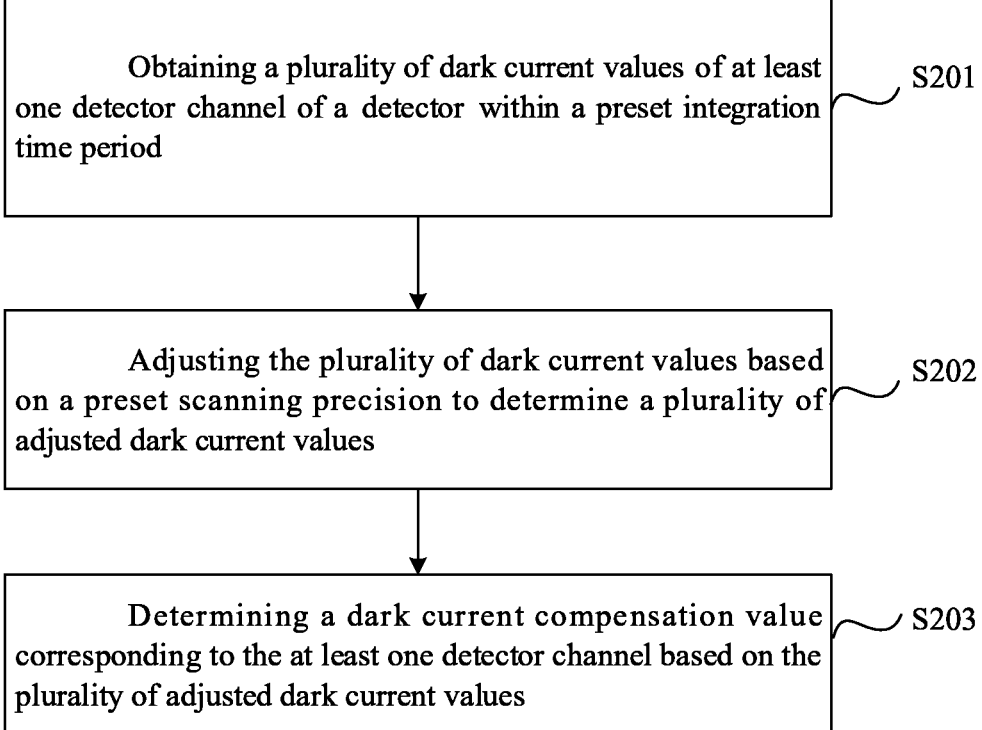
FIG. 2 is a flow chart of a data processing method for a detector of a medical device according to an embodiment of the present disclosure.

A data processing method for a detector of a medical device according to embodiments of the present disclosure is provided. As shown in FIG. 2 which is a flow chart of the data processing method for a detector of a medical device, the method includes the following steps S201-S203.

In the step S201, a plurality of dark current values in a digital circuit within a preset time period is obtained.

The time period can be understood as an exposure time period. For example, a time period of 1 ms means that the time for the detector to receive photons is 1 ms. Therefore, the longer the time period, the higher the energy is. The preset time period is a preset scanning parameter of the detector. In an optoelectronic device, the dark current refers to a reverse DC current generated in a device under a reverse bias condition in the absence of incident light. In the present embodiment, taking a CT device as an example, the dark current value is a digital signal corresponding to scanning data obtained by the CT detector in the absence of X-ray irradiation. In the CT detector, the presence of the dark current value may cause a noise in the real-time scanning data obtained by the CT detector, resulting in artifacts in the final CT image. In some embodiments, the preset time period may be an integration time period.

Specifically, the scanning parameter of the CT detector may be set first, and then the real-time data obtained by the scanning of the CT detector in the absence of X-ray irradiation may be obtained. The real-time data is then converted into a digital signal by the analog-to-digital converter, and the digital signal is output as the dark current value.

In the step S202, the plurality of dark current values in the digital circuit are adjusted based on a preset scanning precision to determine a plurality of adjusted dark current values.

The preset scanning precision is a preset data precision value. For binary data, for example, the data precision value may be 10-bits. The specific value can be determined by staff according to actual conditions. It should be noted that in the present embodiment, the numerical precision of the obtained dark current value is less than the preset scanning precision, for example, the numerical precision of the dark current value is N-bits, and the preset scanning precision is (N+n)-bits, where N and n are each a positive integer.

Specifically, during the adjustment, the numerical precision of each obtained dark current value is adjusted according to the preset scanning precision so that the numerical precision is consistent with the preset scanning precision.

In the step S203, a dark current compensation value corresponding to the at least one detector channel is determined based on the plurality of adjusted dark current values.

The dark current compensation value is configured to optimize the scanning data of the medical device, which eliminates the artifact in the medical image caused by the dark current value.

Specifically, after the plurality of adjusted dark current values are obtained, the plurality of the adjusted dark current values can be averaged to obtain a corresponding dark current compensation value.

According to the data processing method for a detector of a medical device, the plurality of dark current values within the preset time period can be obtained. The preset scanning precision is then obtained, and the plurality of dark current values are adjusted based on the preset scanning precision to determine the plurality of adjusted dark current values. The dark current compensation value corresponding to the at least one detector channel is determined based on the plurality of adjusted dark current values. The numerical precision of the dark current compensation value is thereby improved.

In some embodiments, the above-described method is performed for different detector channels, using the same preset scanning precision, and it is thus ensured that the dark current compensation values corresponding to different detector channels are identical, and meanwhile, the numerical precision of the dark current compensation value is improved, avoiding the impact of the differences among the numerical value precisions of the dark current values corresponding to different detector channels on the medical image. The artifact in the medical image caused by the dark current is thus eliminated, improving the imaging quality of the medical image.

In the case where compensations are performed for multiple detector channels respectively and two or more of the multiple detector channels have different actual scanning precisions, the preset scanning precision may be larger than at least one of the actual scanning precisions of the two or more detector channels. Alternatively, the preset scanning precision may be equal to the largest one of the actual scanning precisions of the two or more detector channels.

In some embodiments, adjusting the plurality of dark current values based on the preset scanning precision to determine the plurality of adjusted dark current values includes determining an actual scanning precision based on the dark current values, determining a correction parameter indicative of the number of bits by which the numerical value is shifted based on the preset scanning precision and the actual scanning precision, and adjusting the plurality of dark current values based on the correction parameter to obtain the plurality of adjusted dark current values. The actual scanning precision is equal to the numerical precision of the dark current value.

For example, when the current scanning precision of the plurally of detector channels is 5-bits, and the preset scanning precision is 8-bits, then the number of bits to be shifted is 3 bits, i.e., the correction parameter is 3. The dark current values can be adjusted respectively such that the numerical precision of each of the dark current values reaches 8-bits.

In the present embodiment, the dark current value is adjusted according to the preset scanning precision and the actual scanning precision, which improves the numerical precision of the dark current values, and provide a data basis for subsequent determination of the dark current compensation value.

In some embodiments, adjusting the plurality of dark current values based on the correction parameter to obtain the plurality of adjusted dark current values includes shifting the plurality of dark current values respectively to a higher bit position based on the correction parameter to obtain the plurality of adjusted dark current values. In other words, low-order bits of zero are added to the plurality of dark current values respectively to obtain the plurality of adjusted dark current values. The number of the low-order bits of zero is equal to the correction parameter.

Exemplarily, the above correction parameter is 3, for example, in the specific correction, each dark current value may be shifted by 3 bits to a higher bit position, and the low bits may be set as 0. For example, if there are two detector channels and the obtained dark current value is 00101 and 00100 respectively, the corresponding adjusted dark current values after the shift are 00101000 and 00100000 respectively.

It should be noted that the processing of the dark current values in the embodiments of the present disclosure is completed in a front-end digital circuit, and the dark current values are not inputted into the computer system for processing, so as to reduce the computational process.

In the present embodiment, by shifting the dark current value according to the correction parameter, the numerical precision of the dark current values is improved. The obtained dark current values of the plurality of detector channels retain more useful information for the subsequent calculation of the dark current compensation value, which is beneficial to subsequently obtaining high-quality medical images.

In some embodiments, determining the dark current compensation value corresponding to the preset time period based on the plurality of adjusted dark current values includes determining an average value of the plurality of adjusted dark current values and determining the dark current compensation value according to the average value.

Specifically, the plurality of adjusted dark current values are averaged after the plurality of adjusted dark current values are obtained to determine the average value of the dark current value as the dark current compensation value.

Exemplarily, taking the adjusted dark current values 00101000 and 00100000 described above as an example, the corresponding average value is 00100100, i.e., the dark current compensation value is 00100100. In contrast, in the case where the dark current values are not shifted, an obtained average value is 00100.1, and a corresponding dark current compensation value is 00100 as the numerical value at the lowest bit is removed, resulting in a decrease in the precision of the dark current compensation value, and thus causing a compensation error.

Figure 3:
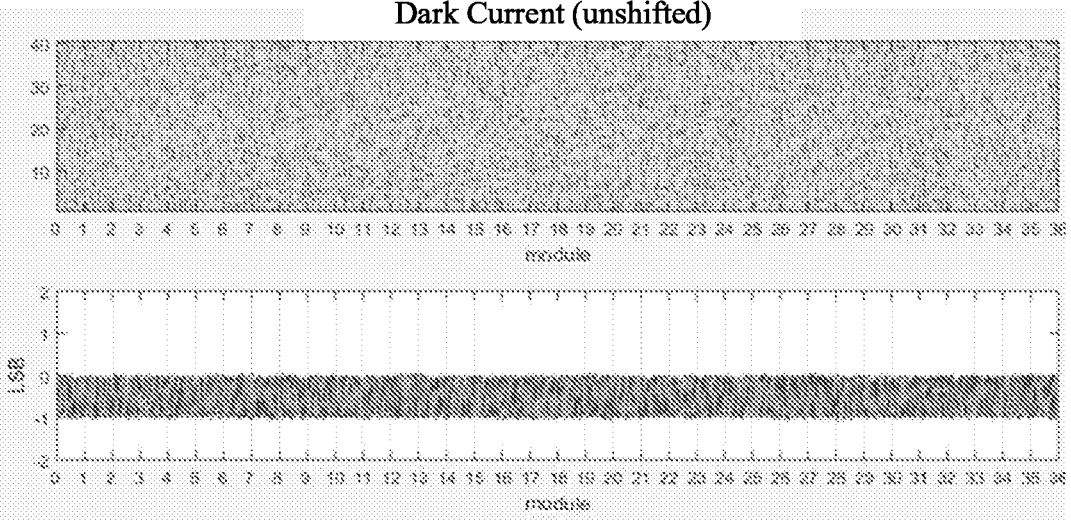
FIG. 3 is a normalized distribution diagram of a plurality of unadjusted dark current values according to an embodiment of the present disclosure.
Figure 4:
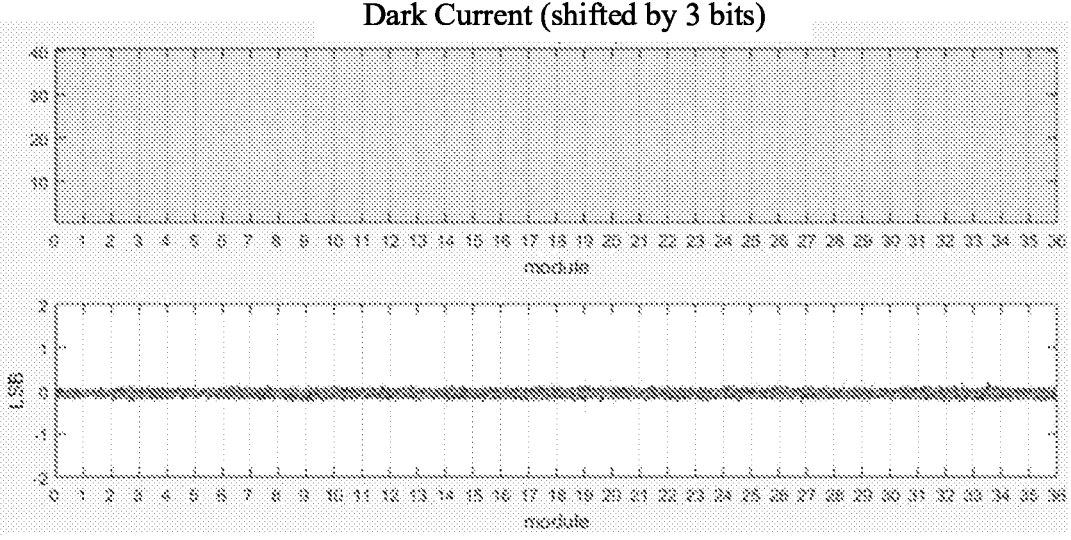
FIG. 4 is a normalized distribution diagram of a plurality of adjusted dark current values according to an embodiment of the present disclosure.

FIG. 3 is a normalized distribution diagram of a plurality of unadjusted dark current values in an embodiment, and FIG. 4 is a normalized distribution diagram of a plurality of adjusted dark current values in an embodiment. From the distributions shown in FIGS. 3 and 4, it is apparent that there is less difference in the dark current distributions of different detector channels and a higher degree of normalization is achieved, if the shift process is performed.

In the present embodiment, an average condition of all the data values is determined by calculating the average value of a plurality of adjusted dark current values, and errors between different detector channels are fully considered. The dark current compensation value is determined according to the average value, which is beneficial to the subsequent unified compensation of scanning data for all the channels, and further provides a data basis for subsequent elimination of the dark current interference in scanning data while simplifying the calculation process.

In some embodiments, obtaining the plurality of dark current values within the present time period includes obtaining a plurality of output data value of a detector channel under a non-exposure condition, and performing analog-to-digital conversion of the plurality of output data values to obtain the plurality of dark current values.

The non-exposure state refers to, for example, a condition of no X-ray irradiation. Exemplarily, in a CT detector, after presetting the CT detector, a plurality of CT detectors corresponding to different channels may be activated to perform scan without the x-ray irradiation, thereby obtaining a plurality of dark current values.

It should be noted that the non-exposure state in the present embodiment may also be a condition of no light irradiation commonly used by other medical devices, such as γ-ray or ultrasonic wave irradiation.

In the present embodiment, a plurality of dark current values corresponding to different detector channels in the non-exposure state are obtained, and a leakage current of a photoelectric element corresponding to the current detector can be accurately determined, such that the interference of the dark current value to the scanning data can be eliminated during the subsequent scanning.

In some embodiments, after determining the dark current compensation value corresponding to the at least one detector channel based on the plurality of adjusted dark current values, the method further includes obtaining scanning data values, determining adjusted scanning data values based on the scanning data values and the dark current compensation value, and performing an image reconstruction based on the adjusted scanning data values to obtain a scanning image.

In some embodiments, the scanning data may be real-time scanning data. Alternatively, the scanning data may be obtained in advance, e.g., prestored scanning data. Real-time scanning data is taken as an example in the following illustration. Correspondingly, the scanning image obtained based on the real-time scanning data is a real-time scanning image.

It should be noted that the numerical precision of the real-time scanning data in the present embodiment is equal to the actual scanning precision, i.e., the real-time scanning data values and the dark current values have the same numerical precision. Therefore, before the real-time scanning data values are corrected, the numerical precision of the real-time scanning data values needs to be adjusted according to the preset scanning precision, so that the adjusted numerical precision of the real-time scanning data values is identical to the numerical precision of the dark current compensation value. The specific adjustment process of the numerical precision is the same as that of the dark current value as described above. Exemplarily, when the preset scanning precision is 8-bits and the real-time scanning data value is 10011, the corresponding adjusted real-time scanning data value is 10011000.

The real-time scanning data values may be corrected according to the dark current compensation value after the real-time scanning data value are adjusted, to obtain corrected real-time scanning data values. Then, the computer system may perform the image reconstruction according to the corrected real-time scanning data values to obtain a corresponding real-time scanning image. The corrected real-time scanning data values can be directly used for the image reconstruction. Alternatively, before being used for image reconstruction, the corrected data can be restored to its original precision.

Figure 5:
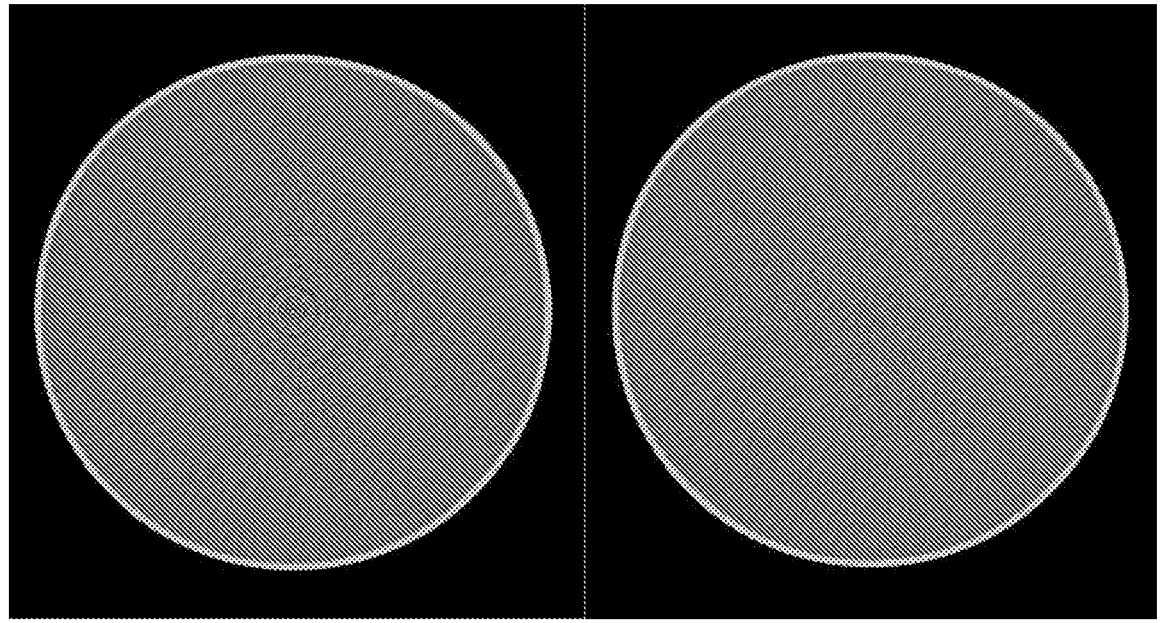
FIG. 5 is a comparison diagram of CT images corresponding to an unadjusted dark current and an adjusted dark current value respectively according to an embodiment of the present disclosure.

FIG. 5 shows a comparison between a CT image corresponding to unadjusted dark current values and a CT image corresponding to adjusted dark current values in an embodiment. As shown in FIG. 5, the left diagram shows a CT image corresponding to the unadjusted dark current values, and the right diagram shows a CT image corresponding to the adjusted dark current values. Obviously, as shown in FIG. 5, the ring artifact is eliminated in the corresponding CT image obtained under the condition that the dark current values are adjusted, and the image quality is significantly improved.

In the present embodiment, the real-time scanning data values are corrected based on the dark current value, thereby eliminating the interference of the dark current to the real-time scanning data values, improving the data precision during the image reconstruction. The final imaging quality is thus improved because the ring artifact is eliminated in the CT image.

In some embodiments, determining the corrected real-time scanning data values based on the real-time scanning data values and the dark current compensation value includes performing a differencing correction on the real-time scanning data values based on the dark current compensation value to determine the corrected real-time scanning data values.

It should be understood that during the actual scanning process, the obtained real-time scanning data values may be mixed with dark current values, resulting in artifacts in the medical image obtained based on the real-time scanning data values. Accordingly, it is required to process the real-time scanning data values before the image reconstruction to eliminate the interference of the dark current values. Specifically, the dark current compensation value is subtracted from the adjusted real-time scanning data values, and then the corrected real-time scanning data values are output.

In the present embodiment, after the real-time scanning data values are obtained, the dark current compensation value is subtracted from the real-time scanning data values respectively, and the corrected real-time scanning data values available for image reconstruction are thus obtained, avoiding the interference of the dark current values to the image during the subsequent image reconstruction, and improving the image quality.

Figure 6:
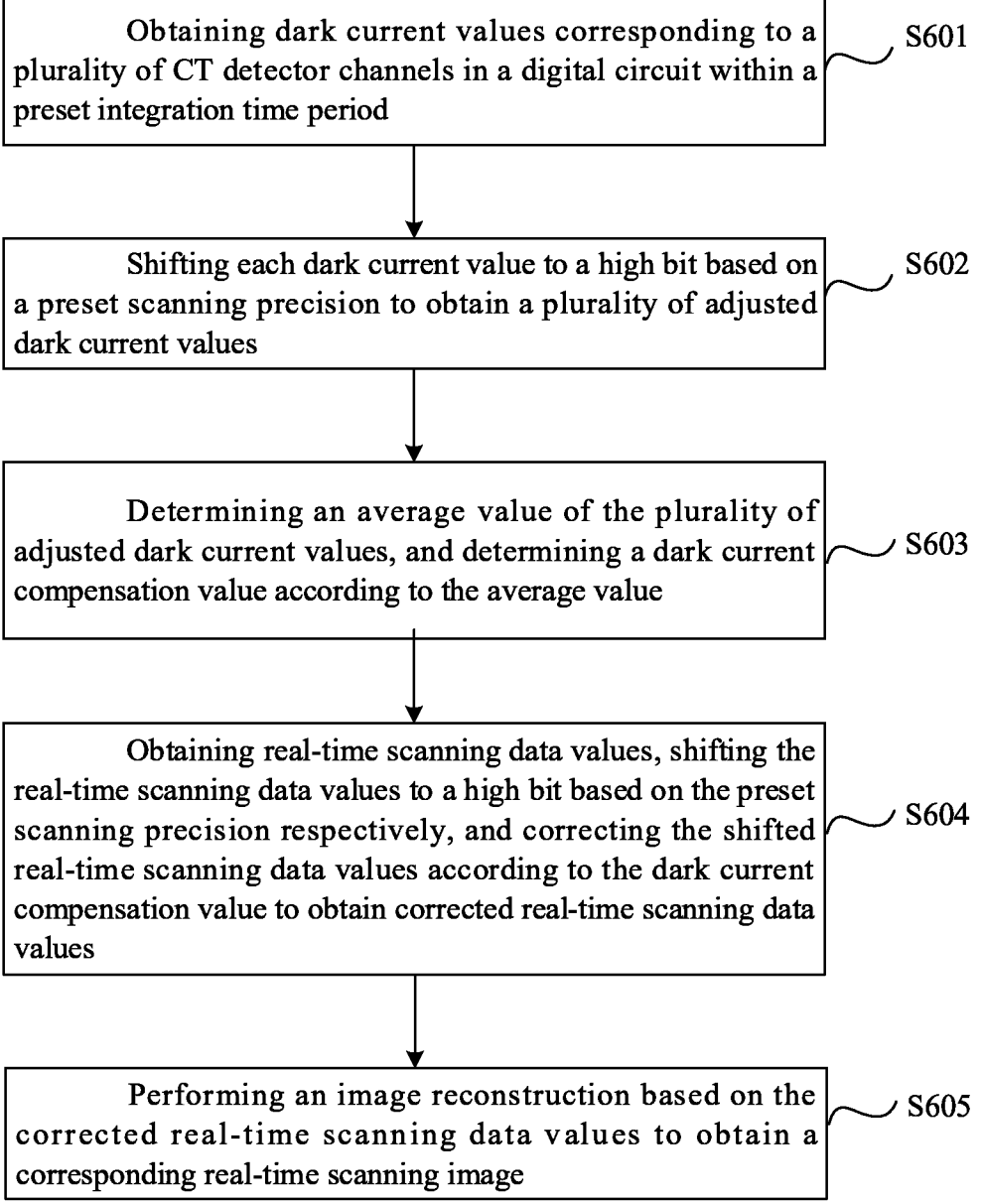
FIG. 6 is a flow chart of a data processing method for a CT detector digital circuit according to an embodiment of the present disclosure.

FIG. 6 is a flow chart showing a data processing method for a digital circuit of a CT detector according to an embodiment. As shown in FIG. 6, the method includes the following steps S601-S605.

In the step S601, dark current values corresponding to a plurality of CT detector channels in a digital circuit within a preset time period are obtained.

In the step S602, each dark current value is shifted to a higher bit position based on a preset scanning precision to obtain a plurality of adjusted dark current values.

In the step S603, an average value of the plurality of adjusted dark current values is determined, and a dark current compensation value is determined according to the average value.

In the step S604, real-time scanning data values are obtained, the real-time scanning data values are shifted to a higher bit position based on the preset scanning precision, respectively, and the shifted real-time scanning data values are corrected according to the dark current compensation value to obtain corrected real-time scanning data values.

In the step S605, an image reconstruction is performed based on the corrected real-time scanning data values to obtain a corresponding real-time scanning image.

In the present embodiment, the obtained plurality of dark current values are shifted to obtain a corresponding plurality of adjusted dark current values, and the dark current compensation value is determined based on the adjusted dark current values. The real-time scanning data values are corrected based on the compensation value, and finally, the image reconstruction is performed based on the corrected real-time scanning data values. By adjusting the numerical precision of the dark current values, it is ensured that the dark current compensation values corresponding to different CT detector channels are consistent, and meanwhile, the numerical precision of the dark current compensation value is improved, thereby avoiding the impact of the difference between the numerical precisions of the dark current value corresponding to different detector channels on CT imaging. The artifact in the CT image caused by the dark current is thus eliminated, and the imaging quality of the CT image is thus improved.

It should be noted that the CT detector in the CT scanner described above is only one exemplary embodiment. In other embodiments, the detector of the medical device may also be a photoelectric detector in a digital radiography (DR) imaging device, a computed radiography (CR) device, a positron emission computed tomography (PET) device, or other medical imaging devices.

Exemplary, in the DR device and the CR device, the dark current value is scanning data under the condition of no X-ray irradiation. The dark current value in the PET device may be scanning data obtained under the condition of no positron emission.

It is to be understood that although the various steps in the flowcharts involved in various aforementioned embodiments are displayed in sequence as indicated by the arrows, these steps are not necessarily performed in sequence in the order indicated by the arrows. Unless expressly stated herein, the execution of these steps is not strictly restrictive and may be performed in other order. Moreover, at least a part of the steps in the flowcharts involved in various aforementioned embodiments may include a plurality of steps or a plurality of stages, which are not necessarily performed at the same moment, but may be executed at different moments, and the order of execution of these steps or stages is not necessarily performed sequentially, but may be performed alternately or alternately with other steps or at least a part of the steps or stages of other steps.

Based on the same inventive concept, according to embodiments of the present disclosure, a data processing apparatus for a detector digital circuit is provided, which is configured to implement the above-mentioned data processing method for the digital circuit of the detector of the medical device. The solution for solving the problem provided by the apparatus is similar to the solution of the above-mentioned method. Accordingly, for the specific limitations on the data processing apparatus for the detector of the medical device in one or more embodiments provided below, reference can be made to the limitations on the data processing method for a detector of a medical device described above, which will not be repeated here.

Figure 7:
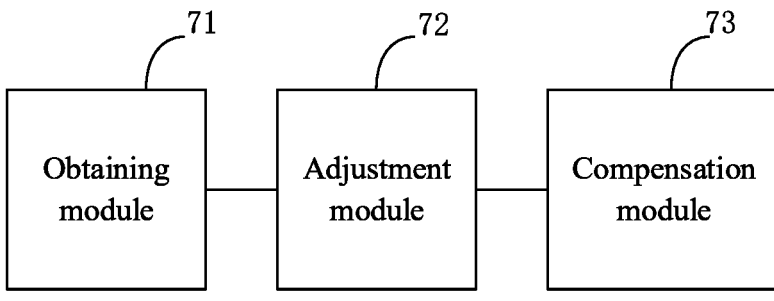
FIG. 7 is a block diagram of a structure of a data processing apparatus for a detector of a medical device according to an embodiment of the present disclosure.

In an embodiment, as shown in FIG. 7, a data processing apparatus for a detector of a medical device is provided, which includes an obtaining module 71, an adjustment module 72, and a compensation module 73.

The obtaining module 71 is configured to obtain a plurality of dark current values in a digital circuit within a preset time period.

The adjustment module 72 is configured to obtain a preset scanning precision, adjust the plurality of dark current values based on the preset scanning precision, and determine a plurality of adjusted dark current values.

The compensation module 73 is configured to determine a dark current compensation value corresponding to the at least one detector channel based on the plurality of adjusted dark current values.

In the above-mentioned apparatus, a plurality of dark current values within the present time period are obtained. A preset scanning precision is then obtained. The plurality of dark current values are adjusted based on the preset scanning precision to determine a plurality of adjusted dark current values. A dark current compensation value corresponding to the at least one detector channel is determined based on the plurality of adjusted dark current values. By adjusting the numerical precision of the dark current value, it is ensured that the dark current compensation values corresponding to different CT detector channels are consistent, and meanwhile, the numerical precision of the dark current compensation value is improved, thereby avoiding the impact of the difference between the numerical precisions of the dark current values corresponding to different detector channels on CT imaging. The artifact in the CT image caused by the dark current is thus eliminated, and the imaging quality of the CT image is thus improved.

Further, the adjustment module 72 is configured to determine an actual scanning precision based on the dark current values, determine a correction parameter based on the preset scanning precision and the actual scanning precision, and adjust the plurality of dark current values based on the correction parameter to obtain a plurality of adjusted dark current values.

Further, the adjustment module 72 is configured to shift the plurality of dark current values to a higher bit position based on the correction parameter, respectively, to obtain a plurality of adjusted dark current values.

Further, the compensation module 73 is configured to determine an average value of the plurality of adjusted dark current values, and determine the dark current compensation value according to the average value.

Further, the obtaining module 71 is configured to obtain a plurality of output data values of a detector channel under a non-exposure condition, perform an analog-to-digital conversion of the plurality of output data values to obtain the plurality of dark current values.

Further, the compensation module 73 is configured to obtain real-time scanning data values, determine corrected real-time scanning data values based on the real-time scanning data values and the dark current compensation value, and perform an image reconstruction based on the corrected real-time scanning data values to obtain a real-time scanning image.

Further, the compensation module 73 is configured to perform a differencing correction on the real-time scanning data values based on the dark current compensation value to determine the corrected real-time scanning data values.

The various modules in the data processing apparatus for a detector of a medical device mentioned above can be fully or partially implemented through software, hardware, and combinations thereof. The above modules can be embedded in or independent of a processor in a computer device in the hardware form, or stored in a memory in the computer device in the software form so that they can be called and executed by the processor to implement the corresponding operations of the above modules.

Figure 8:
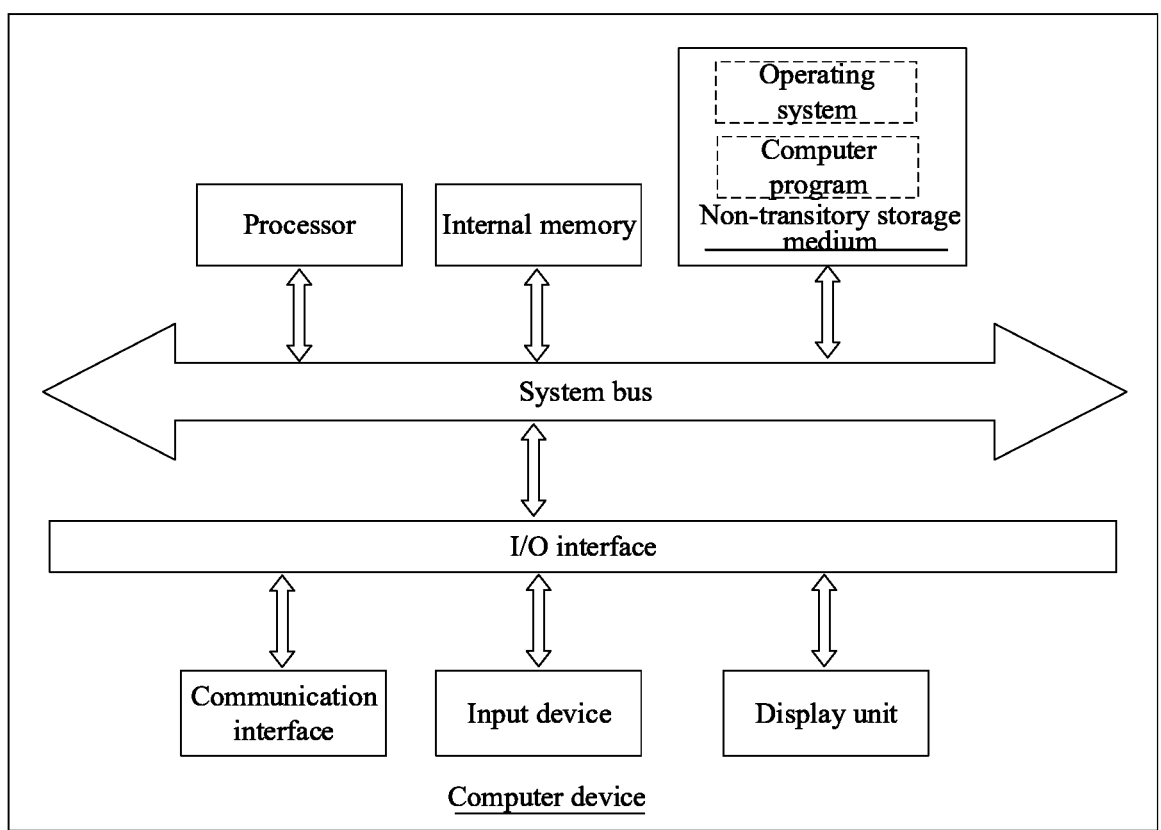
FIG. 8 is an internal structure diagram of a computer device according to an embodiment of the present disclosure.

In an embodiment, a computer device is provided, which can be a terminal, and an internal structure diagram thereof is shown in FIG. 8. The computer device includes a processor, a memory, a communication interface, a display screen, and an input device, which are connected through a system bus. The processor of the computer device is configured to provide computing and control capabilities. The memory of the computer device includes a non-transitory storage medium and an internal memory. The non-transitory storage medium stores an operating system and a computer program. The memory provides an operating environment for the operating system and computer program in the non-transitory storage medium. The communication interface of the computer device is used for wired or wireless communication with an external terminal, which can be achieved through WIFI, mobile cellular networks, Near Field Communication (NFC), or other technologies. The computer program is executed by the processor to implement a data processing method in a CT detector digital circuit. The display screen of the computer device may be a liquid crystal display screen or an electronic ink display screen. The input device of the computer device may be a touch layer covering the display screen, or a key, a trackball or a touch pad provided on the housing of the computer device, or an external keyboard, touch pad or mouse.

Those skilled in the art can appreciate that the structure shown in FIG. 8 is merely a block diagram of a partial structure related to the technical solution of the present disclosure, and does not constitute a limitation on the computer device to which the present disclosure is applied. The specific computer device may include more or fewer components than shown in the figures, or have a combination of certain components, or have a different component arrangement.

In an embodiment, a computer device is provided, which includes a processor and a memory for storing a computer program. The processor, when executing the computer program, performs a data processing method, which includes obtaining a plurality of dark current values in a digital circuit within a preset time period, adjusting the plurality of dark current values based on the preset scanning precision, determining a plurality of adjusted dark current values, and determining a dark current compensation value corresponding to the preset time period based on the plurality of adjusted dark current values.

In other embodiments, the processor, when executing the computer program, further performs the steps of the data processing method for a detector of a medical device according to various embodiments of the present disclosure.

In an embodiment, a computer-readable storage medium is provided, on which a computer program is stored. The computer program, when executed by a processor, causes the processor to perform a data processing method, which includes obtaining a plurality of dark current values in a digital circuit within a preset time period, adjusting the plurality of dark current values based on the preset scanning precision, determining a plurality of adjusted dark current values, and determining a dark current compensation value corresponding to the preset time period based on the plurality of adjusted dark current values.

It should be noted that the user information (including but not limited to user device information, user personal information, etc.) and data (including but not limited to data for analysis, stored data, displayed data, etc.) referred to in this disclosure are all information and data authorized by the user or fully authorized by all parties.

A person of ordinary skill in the art can understand that all or part of the processes in the methods of the above embodiments can be achieved by computer instructions instructing the relevant hardware to do so. The computer instructions can be stored in a non-transitory computer-readable storage medium, and when executed, perform the processes such as those of the methods of the embodiments described above. The memory, database, or other medium recited in the embodiments of the disclosure include at least one of non-transitory and transitory memory. The non-transitory memory includes read-only memory (ROM), magnetic tape, floppy disk, flash memory, optical memory, high density embedded non-transitory memory, resistive memory (ReRAM), magnetoresistive random access memory (MRAM), ferroelectric memory (FRAM), phase change memory (PCM), or graphene memory, etc. The transitory memory includes random access memory (RAM) or external cache memory, etc. For illustration rather than limitation, RAM may be in various forms, such as static random access memory (SRAM) or dynamic random access memory (DRAM), etc. The databases involved in the embodiments of the present disclosure may include at least one of a relational database and a non-relational database. The non-relational databases may include, without limitation, a blockchain-based distributed database, etc. The processors involved in the embodiments of the present application may be general-purpose processors, central processing units, graphics processors, digital signal processors, programmable logicians, quantum computing-based data processing logicians, etc., without limitation.

The technical features of the foregoing embodiments may be freely combined. For brevity, not all possible combinations of the technical features in the foregoing embodiments are described. However, the combinations of these technical features should be included within the scope of this disclosure, if the combinations are not contradictory.

The above-described embodiments express only implementations of the present application, the descriptions of which are specific and detailed, but cannot be construed as a limitation of the scope of the present application. It is noted that for a person of ordinary skill in the art, variations and improvements can be made without departing from the concept of the present application, which all belong to the protection scope of the present application. Therefore, the protection scope of the present application shall be subject to the attached claims.

The invention claimed is:
1. A data processing method for a detector of a medical device, comprising:
    obtaining a plurality of dark current values of at least one detector channel of the detector within a preset time period;

adjusting the plurality of dark current values based on a preset scanning precision to determine a plurality of adjusted dark current values; and determining a dark current compensation value corresponding to the at least one detector channel based on the plurality of adjusted dark current values;

wherein adjusting the plurality of dark current values based on the preset scanning precision to determine the plurality of adjusted dark current values comprises adjusting the plurality of dark current values based on a correction parameter to obtain the plurality of adjusted dark current values;

wherein adjusting the plurality of dark current values based on the correction parameter to obtain the plurality of adjusted dark current values further comprises shifting the plurality of dark current values respectively to a higher bit position based on the correction parameter.

2. The data processing method according to claim 1, wherein determining the correction parameter comprises:

determining an actual scanning precision based on the plurality of dark current values; and determining a correction parameter based on the preset scanning precision and the actual scanning precision.

3. The data processing method according to claim 2, wherein the adjusting the plurality of dark current values based on the correction parameter to obtain the plurality of adjusted dark current values comprises:

adding low-order bits of zero to the plurality of dark current values respectively to obtain the plurality of adjusted dark current values, the number of the low-order bits of zero being equal to the correction parameter.

4. The data processing method according to claim 1, wherein the determining the dark current compensation value corresponding to the at least one detector channel based on the plurality of adjusted dark current values comprises:

determining an average value of the adjusted dark current values, and determining the dark current compensation value according to the average value of the adjusted dark current values.

5. The data processing method according to claim 1, wherein the obtaining the plurality of dark current values within the present time period comprises:

obtaining a plurality of output data values of the at least one detector channel under a non-exposure condition, and performing an analog-to-digital conversion based on the plurality of output data values to obtain the plurality of dark current values.

6. The data processing method according to claim 1, wherein after determining the dark current compensation value corresponding to the preset time period based on the plurality of adjusted dark current values, the data processing method further comprises:

obtaining scanning data values of the at least one detector channel, determining corrected scanning data values based on the scanning data values and the dark current compensation value;

performing an image reconstruction based on the corrected scanning data values to obtain a scanning image.

7. The data processing method according to claim 6, wherein the determining the corrected scanning data values based on the scanning data values and the dark current compensation value comprises:

performing a differencing correction on the scanning data values based on the dark current compensation value to determine the corrected scanning data values.

8. The data processing method according to claim 7, wherein before performing a differencing correction on the scanning data values based on the dark current compensation value, the data processing method further comprises:

adjusting a scanning precision of the scanning data values such that the adjusted scanning precision is consistent with the that of dark current compensation value.

9. The data processing method according to claim 1, wherein the at least one detector channel comprises two or more detector channels with different actual scanning precisions, and the preset scanning precision is larger than at least one of the actual scanning precisions.

10. The data processing method according to claim 9, wherein the preset scanning precision is equal to the largest one of actual scanning precisions.

11. A computer device, comprising a processor and a memory storing a computer program, wherein the processor, when executing the computer program, performs a data processing method, the method comprising:

obtaining a plurality of dark current values of at least one detector channel within a preset time period;

adjusting the plurality of dark current values based on a preset scanning precision to determine a plurality of adjusted dark current values; and determining a dark current compensation value corresponding to the at least one detector channel based on the plurality of adjusted dark current values;

wherein adjusting the plurality of dark current values based on the preset scanning precision to determine the plurality of adjusted dark current values comprises adjusting the plurality of dark current values based on a correction parameter to obtain the plurality of adjusted dark current values;

wherein adjusting the plurality of dark current values based on the correction parameter to obtain the plurality of adjusted dark current values further comprises shifting the plurality of dark current values respectively to a higher bit position based on the correction parameter.

12. The computer device according to claim 11, wherein determining the correction parameter comprises:

determining an actual scanning precision based on the plurality of dark current values;

determining a correction parameter based on the preset scanning precision and the actual scanning precision.

13. The computer device according to claim 12, wherein the adjusting the plurality of dark current values based on the correction parameter to obtain the plurality of adjusted dark current values comprises:

adding low-order bits of zero to the plurality of dark current values respectively to obtain the plurality of adjusted dark current values, the number of the low-order bits of zero being equal to the correction parameter.

14. The computer device according to claim 11, wherein the determining the dark current compensation value corresponding to the at least one detector channel based on the plurality of adjusted dark current values comprises:

determining an average value of the adjusted dark current values, and determining the dark current compensation value according to the average value of the adjusted dark current values.

15. The computer device according to claim 11, wherein the obtaining the plurality of dark current values within the present time period comprises:

obtaining a plurality of output data values of the at least one detector channel under a non-exposure condition, and performing an analog-to-digital conversion based on the plurality of output data values to obtain the plurality of dark current values.

16. The computer device according to claim 11, wherein after determining the dark current compensation value corresponding to the preset time period based on the plurality of adjusted dark current values, the data processing method further comprises:

obtaining scanning data values of the at least one detector channel, determining corrected scanning data values based on the scanning data values and the dark current compensation value;

performing an image reconstruction based on the corrected scanning data values to obtain a scanning image.

17. The computer device according to claim 16, wherein the determining the corrected scanning data values based on the scanning data values and the dark current compensation value comprises:

performing a differencing correction on the scanning data values based on the dark current compensation value to determine the corrected scanning data values.

18. The computer device according to claim 17, wherein before performing a differencing correction on the scanning data values based on the dark current compensation value, the data processing method further comprises:

adjusting a scanning precision of the scanning data values such that the adjusted scanning precision is consistent with the that of dark current compensation value.

19. The computer device according to claim 11, wherein the at least one detector channel comprises two or more detector channels with different actual scanning precisions, and the preset scanning precision is larger than at least one of the actual scanning precisions or equal to the largest one of actual scanning precisions.

20. A non-transitory computer-readable storage medium having stored therein a computer program, wherein the computer program, when executed by a processor, causes the processor to perform a data processing method according to claim 1.

\* \* \* \* \*